United States Patent [19]

Atwood

[11] Patent Number: 4,921,924
[45] Date of Patent: May 1, 1990

[54] ISOPRENE RECOVERY IN THE BUTYL RUBBER PROCESS

[75] Inventor: Harvey E. Atwood, Kingwood, Tex.

[73] Assignee: Exxon Chemical Patents Inc., Linden, N.J.

[21] Appl. No.: 922,679

[22] Filed: Oct. 24, 1986

Related U.S. Application Data

[63] Continuation of Ser. No. 814,097, Dec. 27, 1985, abandoned.

[51] Int. Cl.$^5$ .................................................. C08F 6/10
[52] U.S. Cl. .................................... 526/339; 528/500; 210/690
[58] Field of Search .................. 526/339; 528/500; 210/690

[56] References Cited

U.S. PATENT DOCUMENTS

| | | | |
|---|---|---|---|
| 2,347,945 | 5/1944 | Frey | 260/683.4 |
| 2,356,128 | 8/1944 | Thomas | 526/339 |
| 2,356,129 | 8/1944 | Sparks | 526/339 |
| 2,391,149 | 12/1945 | Frey | 196/41 |
| 2,412,220 | 12/1946 | Ibach et al. | 196/41 |
| 3,862,900 | 1/1975 | Reusser | 208/262 |
| 3,864,243 | 2/1975 | Reusser et al. | 208/262 |
| 4,020,117 | 4/1977 | Sisson | 260/652 P |
| 4,198,265 | 4/1980 | Johnson | 528/499 |

FOREIGN PATENT DOCUMENTS

| | | |
|---|---|---|
| 2839516 | 3/1980 | Fed. Rep. of Germany . |
| 506597 | 6/1976 | U.S.S.R. . |
| 1438246 | 6/1976 | United Kingdom . |

Primary Examiner—Paul R. Michl
Assistant Examiner—Mark R. Buscher

[57] ABSTRACT

A method for removing a tertiary halide from an olefin hydrocarbon stream which comprises contacting the hydrocarbon stream with activated alumina at a temperature of about −40° to about 120° C.

14 Claims, 1 Drawing Sheet

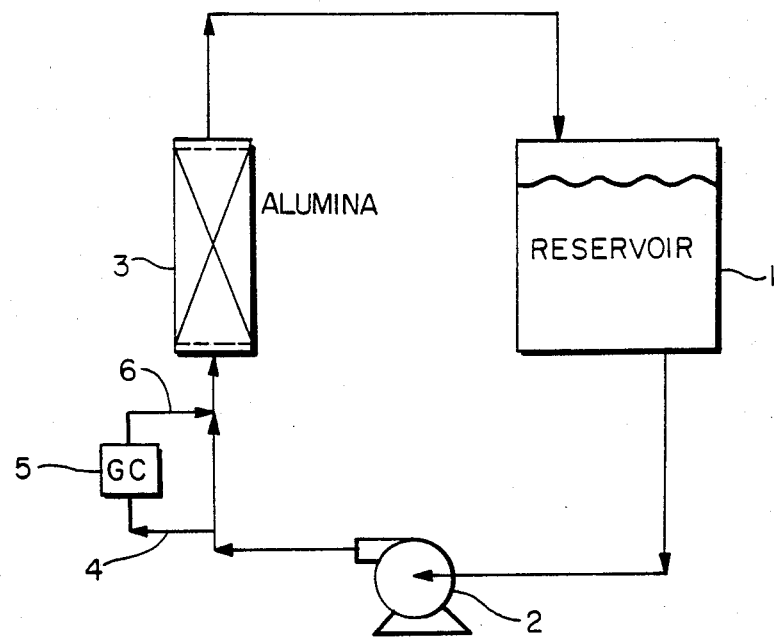

ISOPRENE RECOVERY IN THE BUTYL RUBBER PROCESS

This is a continuation, of application Ser. No. 814,097, filed 12/27/85, now abandoned.

BACKGROUND OF THE INVENTION

Butyl rubber was one of the earlier synthetic rubbers to be developed. It is a copolymer of isobutylene and a conjugated multiolefin, usually isoprene. It was long recognized that the isoprene could not be recycled in the butyl rubber process because the recycled monomer stream acted as a poison to the polymerization process. It was not until after a substantial number of years of discarding isoprene that the cause of this poisoning effect was understood. It is not known that the poisoning effect is the result of the formation of t-butyl chloride (t-BCl) from isobutylene reactions with the HCl. The t-butyl chloride tends to concentrate by fractionation in the recycle isoprene stream and affects the polymerization by chain transfer mechanisms so that lower molecular weight copolymers ar produced.

Since t-butyl chloride and isoprene cannot easily be separated from one another by standard fractionation techniques, butyl rubber plants continue to discard the unreacted isoprene which has been used in the butyl rubber process rather than recycling it. The result is a significant increase in polymerization costs. For example, in a 50,000 ton/yr. butyl rubber plant, isoprene recovery would reduce isoprene raw material costs by about $600,000 per year.

Many techniques are known for removing halides from process streams. For example, in the production of methyl chloride and methylene chloride by the (oxy) chlorination of methane, the chlorides can be recovered by gas phase adsorption in beds of adsorbed materials including silica gels, activated carbon, activated alumina, molecular sieves, or their combinations; see U.S. Pat. No. 4,020,117. The adsorption is carried out at about $-50°$ C. to about $20°$ C. The adsorbed halides are stripped from the adsorption stage at about $100°-400°$ C. Similarly, German patent No. 2,839,516 discloses a process for purifying an exhaust gas stream to remove contaminants such as halogens or halogenated hydrocarbons by passing the gas through alumina or calcium compounds.

British Patent No. 1,438,246 discloses a process for reacting a chloroform process stream containing impurities by contacting the stream in the vapor phase with activated carbon or alumina. It is alleged that $CH_2ClBr$ which is present as an impurity in the chloroform, reacts with the chloroform to form $CHCl_2Br$ and $CH_2Cl_2$, which are then readily separated from the chloroform by distillation.

Soviet Union patent No. 506,597 teaches the purification of recycled methylene chloride-isobutylene stream by passing the compounds first in the vapor phase over alumina and then in the liquid phase at $10°$ to $20°$ C. It is disclosed that the process removes water, dimethyl ether, and HCl from the stream.

U.S. Pat. No. 2,347,945 discloses a method for removing organic fluorides from a hydrocarbon stream either in the liquid or gaseous phase by contacting the stream with a "contact material." The contact material can be alumina, hydrated bauxite, chromium oxide, and metals from the iron groups, especially nickel deposited on an inert support.

U.S. Pat. No. 3,864,243 discloses a process for the removal of combined chlorine (organic or inorganic) from a hydrocarbon stream by percolating the hydrocarbon through a bed of dehydrated activated alumina, e.g. bauxite. The adsorption process is said to be more effective at room temperature than at elevated temperatures, e.g., $98°$ C. Similarly, U.S. Pat. No. 3,862,900 discloses the room temperature adsorption of organic halides on molecular sieves (pore size 7–11 A).

U.S. Pat. No. 2,412,220 discloses a process for the removal or organic fluorides from a hydrocarbon stream by passing the hydrocarbon through a bed of alumina which is catalytically active for hydrogenation or dehydrogenation. It is alleged that the effluent stream contains silicon fluorides which are subsequently removed by treating the hydrocarbon stream with an alkali metal hydroxide, e.g., NaOH, and then filtering the hydrocarbon stream through a non-siliceous granular filter medium, e.g., charcoal. In a similar vein, U.S. Pat. No. 2,391,149 discloses the removal of fluorides from a hydrocarbon stream by contacting the hydrocarbon with alumina which has been impregnated with an alkali metal hydroxide.

While the art generally teaches the use of materials such as activated carbon and alumina for the purification of halide containing process streams, it is apparent from these disclosures that not all organic halides are removed from a process stream contacted with these and other materials of the prior art. Furthermore, there is no disclosure of the removal of t-butyl chloride from such hydrocarbon streams; nor is there any teaching from which it could be concluded that a particular contact medium is preferred over others for the removal of t-butyl chloride from an isoprene stream.

SUMMARY OF THE INVENTION

It has surprisingly been found that a recovery stream of isoprene from a butyl rubber polymerization process can be purified by treatment with alumina. The resulting treated isoprene can be recycled for use in the butyl rubber process.

In a preferred embodiment, the hydrocarbon stream is contacted with the alumina at a temperature of about $40°$ C. to about $80°$ C. Surprisingly, the elevated temperature results in an improvement in halide removal.

BRIEF DESCRIPTION OF THE DRAWING

The drawing is a schematic of the Dynamic Experimental System used in the dynamic experiments.

DETAILED DESCRIPTION

Butyl rubber is a copolymer of an isoolefin and a conjugated multiolefin. The useful copolymers comprise a major portion of an isoolefin and a minor amount, preferably not more than 30 wt %, of a conjugated multiolefin. The preferred copolymers comprise about 85–99.5 wt % (preferably 95–99.5 wt %) of isoolefin and about 15–0.5 wt % (preferably about 5–0.5 wt %) of a multiolefin of about 4–14 carbon atoms. These copolymers are referred to in the patents and literature as "butyl rubber"; see, for example, the textbook Synthetic Rubber by G. S. Whitby (1954 edition by John Wiley and Sons, Inc.), pages 608–609, etc. The term "butyl rubber" as used in the specification and claims includes the aforementioned copolymers of an isoolefin having 4–7 carbon atoms and about 0.5 to 20 wt % of a conjugated multiolefin of about 4–10 carbon atoms. Preferably these copolymers contain about 0.5 to about 5% conjugated multiolefin. Suitable conjugated multiolefins include isoprene, butadiene, dimethyl butadiene, piperylene, etc. The preferred isoolefin is isobutylene.

Commercial butyl rubber is a copolymer of isobutylene and minor amounts of isoprene. It is generally prepared in a slurry process using methyl chloride as a polymerization diluent and a Friedel-Crafts catalyst as the polymerization initiator. The methyl chloride diluent offers the advantage that $AlCl_3$, a relatively inexpensive Friedel-Crafts catalyst is soluble in it, as are the isobutylene and isoprene comonomers. Additionally, at the polymerization temperature, the butyl rubber polymer is insoluble in the methyl chloride and precipitates out of solution as fine particles. The polymerization is generally carried out at temperatures of about $-90°$ C. to $-100°$ C. See U.S. Pat. Nos. 2,356,128 and 2,356,129 incorporated herein by reference.

The polymerization process which is carried out in a draft tube reactor is continuous. Monomer feed and catalyst are continuously introduced to the reactor where an axial flow pump is located. The pump circulates the butyl rubber slurry at high velocity to provide efficient mixing and heat transfer. Polymer slurry containing about 20-30 wt % butyl rubber in methyl chloride continuously overflows from the reactor through a transfer line.

Where the desired product is the butyl rubber itself, the slurry is fed through the transfer line to a flash drum operated at about 140-1180 kpa (1.38-11.58 atm. abs.) and 65°-75° C. Steam and hot water are mixed with the slurry in a nozzle as it enters the flash drum to vaporize methyl chloride and unreacted monomers which pass overhead and are recovered. The polymer-water slurry is finished by water removal and drying.

The methyl chloride and unreacted monomers which have been flashed off are cooled to condense out most of the water. However, this methyl chloride/hydrocarbon stream must be further dried before it can be processed for recycling. The drying is accomplished in an alumina drier. The alumina catalyzes the hydrolysis of methyl chloride forming MeOH and HCl. The HCl reacts with some of the isobutylene to form t-butyl chloride.

The methyl chloride and monomers are separated by standard fractionation techniques. Methyl chloride and isobutylene are recovered and the isoprene has been heretofor discarded because the t-butyl chloride concentrates in the isoprene, and is not readily separated from isoprene by standard fractionation techniques. In the practice of this invention, the dried, recovered isoprene is purified for reuse by treatment with activated alumina.

While a wide variety of compounds will remove halides to some extent from a hydrocarbon stream, activated alumina has been found to be a most effective adsorption medium. The term "activated alumna" as used in the specifications and claims means dehydrated alumina of high surface area, conventionally used in the butyl rubber art among others as a desiccant to remove water from methyl chloride or other streams. Illustrative, non-limiting examples of commercially available material which meets this description of activated alumina are Kaiser 201, ALCOA H-151, and PECHINEY A.

In the practice of this invention, the recovered isoprene stream is contacted with the alumina on a continuous basis using a column packed with alumina. The hydrocarbon is preferably pumped upward through a vertical bed of alumina. It is well within the skill of those in the art to use a modification of this technique for contacting the hydrocarbon stream with the alumina. For example, the hydrocarbon can be passed through the column downward or in several vessels in series. Substantially all of the objectionable halides in the liquid isoprene stream can be removed in a single pass through a bed of alumina at a flow rate of one volume of isoprene to one volume of alumina per hour (i v/v/hr) at 60° C. It is preferred, that the purification process be conducted at temperatures above ambient.

Not wishing to be bound by theory, it is believed that the mechanism of halide removal is a chemiadsorption process. That is, in addition to physical adsorption, a chemical reaction takes place converting the organic halide to other organic compounds, in this case isobutylene, and an inorganic halide. Hence, while decreasing the temperature improves adsorption rate, increasing the temperature increases the chemical reaction rate. Since the rate controlling factor is the chemical reaction, improved results are seen with increasing temperature.

The capacity of alumina for chlorides in the process of this invention is about 3 wt % chloride as chlorine. Unlike a conventional low temperature adsorption process the alumina cannot be regenerated for the purpose of this invention by simple hot gas regeneration. It is necessary to first caustic treat and water wash the alumina. As a consequence, there is a high energy cost associated with the subsequently required water removal step. Because of the high regeneration cost and other considerations, it is often more convenient to discard the spent alumina.

In the practice of this invention, the removal of the halogenated compounds, i.e., t-butyl chloride from the isoprene stream can be accomplished over a wide range of temperatures. The useful temperature range for the halide removal is about $-40°$ C. to a temperature below which cracking or polymerization of the olefinic hydrocarbons or t-BCl occurs, e.g. $-40°$ C. to about 120° C.; preferably about 0° C. to 80° C. However because of the chemisorption nature of the halide removal by alumina, it is preferred that the halide removal be accomplished at an elevated temperature. The halide removal can be effected at about 20° C. to 120° C.; more preferably at about 40° C. to about 100° C.; more preferably about 50° C. to about 80° C., e.g., 60° C. to about 80° C. The improvement in halide removal at elevated temperatures is completely unexpected, and contrary to the art recognized advantage in reducing temperature to improve adsorption. As used in the specification and claims, the term "elevated temperature" means a temperature above 20° C. In a preferred embodiment, the t-BCl removal is accomplished at a temperature of at least 30° C.; more preferably, at least 40° C.

Experiments to demonstrate the effectiveness of alumina in the removal of halides from an isoprene stream were conducted both statically and dynamically. In the static test, isoprene contaminated with t-BCl was contacted with alumina in a vial at a fixed temperature for a time sufficient for the alumina to reach a steady state for t-BCl removal. Liquid samples were analyzed using was chromatography (GC) with a 10 foot by ⅛ inch stainless steel column packed with 5% SP-2100 on 100/120 mesh Supelco port.

The dynamic tests were conducted in a simulated liquid solid batch experiment. Isoprene contaminated with t-BCl was circulated at a high flow rate through a static bed of alumina and back to a reservoir. Because of the high circulation rate as compared to the total volume of the system, the per pass conversion of t-BCl over the alumina bed became small and the liquid composition in the entire system was substantially uniform. As a consequence, the system behaved as a uniformly mixed batch reactor. A schematic of the Dynamic Experimental System is shown in the Figure. Isoprene/t-BCl was circulated from the reservoir, 1, by pump, 2, through an alumina bed, 3, and back to the reservoir, 1. A sample was withdrawn for GC analysis at sample line 4, run through the GC column, 5, and returned to the system through line, 6. The advantages of the instant invention may be more readily appreciated by reference to the following examples.

EXAMPLE 1

A static isoprene purification run was made using PECHINEY type A high surface area alumina beads (size 2-5 mm) which were first heated at 115° C. in a vacuum oven at 29.5" vacuum for 17 hours, and then cooled at 20" vacuum. A t-BCl contaminated isoprene solution was prepared by mixing 4.9 grams (5.80 ml at 23° C.) of t-BCl and 494.6 grams of distilled isoprene. The solution was estimated to contain about 9,810 ppm of t-BCl, but based on GC analysis, the solution contained 11,210 ppm of t-BCl.

A charge of 1.0 gram of $Al_2O_3$ and 20 ml (13.658 g) of the t-BCl/isoprene solution was added to a vial which was then sealed and placed in a constant temperature bath at about $-22$ to $-20°$ C. for 382 hours. GC analysis of the solution after contact with the $Al_2O_3$ showed that the t-BCl concentration dropped from 11,210 to 9223 ppm. This represents removal capacity of 2.71 g of t-BCl per 100 g of alumina, or on an equivalent basis, 1.07 g of HCl per 100 g of alumina. Some isobutylene was found in the solution as a result of the dehydrochlorination reaction of t-BCl on the alumina. The data are summarized in Table I.

EXAMPLE 2

The test procedure of Example I was repeated except that analyses were run only at the beginning and end of the run. GC Analysis after 381 hours of contact time showed a drop in t-BCl concentration from 11,210 to 9,926 ppm. This represents a t-BCl removal capacity of 2.61 g t-BCl/100 g alumina, or on an equivalent basis, 1.03 g HCl/100 g of alumina. Averaging of the results of Examples 1 and 2 gives an average removal capacity at $-22°$ C. of 2.66 g of t-BCl per 100 g of alumina. The results are summarized in Table I.

EXAMPLES 3 TO 6

A series of runs were made employing the same procedure of Example 1 except that Examples 3 and 6 were run at $-12°$ to $-10°$ C. and Example 4 and 5 were run at 23°-25° C. The results, which are summarized in Table I, showed removal capacity of 3.76 g of t-BCl/100 g of alumina at $-10°$ C. and 9.06 g of t-BCl/100 g of alumina at 24° C.

It is apparent from the data of Examples 1-6 that the removal capacity of alumina for t-BCl increases with temperature. Hence, the mode of t-BCl removal is believed to be by a catalytic reaction rather than by physical adsorption.

EXAMPLE 7

A t-BCl contaminated solution of isoprene was prepared by combining 8.51 of t-BCl, 752.45 g of redistilled isoprene, and 1.37 g HPLC grade n-heptane which served as an internal standard for GC analysis. The solution has a calculated t-BCl content of 11,163 ppm and 1,797 ppm n-heptane by weight. A 5 cc sample of this solution was reserved for GC analysis. The remaining 757 g were charged to the reservoir of the Dynamic Experimental System (DES). The alumina bed contained 37.5 grams of alumina.

At the beginning of the run the system was pressurized to 200 Kpa and the pump was started. The liquid circulated around the system but bypassed the alumina bed unit. The liquid heated up to 60° C. at which point it was switched to pass through the alumina bed and the removal of t-BCl began. On line GC analyses were performed periodically. After 67 hours on stream the test was stopped although the t-BCl concentration continued to drop. Analysis showed that the t-BCl content dropped from 11,162 to 554 ppm. That represents an equivalent of 21.42 g of t-BCl removal per 100 g of alumina at 60° C.

The system was emptied and 960 cc of solution recovered. The system was then washed with heptane. Solution for a second charge was prepared by combining 8.51 g of t-BCl, 712.72 g of isoprene and 1.37 g of n-heptane. The calculated t-BCl was 11,777 ppm and heptane concentration was 1,896 ppm n-heptane. However, as a result of contamination from the first test described above and heptane trapped in the system, the composition of the solution at the beginning of the second 60° C. run was 11,290 ppm of t-BCl, 30,620 ppm n-heptane, 135 ppm diisobutylene, 13 ppm of isobutylene and 200 ppm diisoprene.

The second run at 60° C. was run under the same conditions as run #1, but the same alumina was used. After 86 hours of contact with the alumina the GC analysis showed a t-BCl content of 4,554 ppm. Hence, the alumina bed had removed an additional 12.93 of t-BCl per 100 g of alumina. The total removal capacity of the alumina was, therefore, 34.35 g t-BCl per 100 g of alumina, or on a equivalent basis, 13.53 g of HCl per 100 g of alumina at 60° C. The results of Example 7 are summarized in Table I.

EXAMPLE 8

The experiment of Example 7 was repeated at 32° C. using a mixture of 8.51 of t-BCl, 755.12 of isoprene, and 1.37 of n-heptane. The solution was found to have 11,125 ppm t-BCl, 4,123 ppm n-heptane, 17 ppm isobutylene, and 60 ppm of diisoprene by GO analysis. The alumina bed was again packed with 37.5 g of fresh alumina. The t-BCl concentration reached a steady state after 96 hours on stream. GC analysis showed that the t-BCl concentration had dropped to 2,900 ppm which is equivalent to 16.78 g of t-BCl per 100 g of alumina or 6.61 g of HCl per 100 g of alumina The results are summarized in Table I.

EXAMPLE 9

After the test of Example 8 was completed, the system temperature was raised to 43° C. and the solution was again recycled through the aluminum bed. The t-BCl level was further lowered from 2,900 ppm to 410 ppm. This represents an additional t-BCl removal of 5.08 g of t-BCl per 100 g of a lumina, and brought the a lumina total adsorption capacity at 43° C. to 21.86 g of t-BCl or 8.61 g of HCl per 100 g of alumina.

Surprisingly, not withstanding the fact that the alumina had become saturated with t-BCl at 82° C., as evidenced by the achievement of a steady state of t-BCl level, increasing the temperature of the system resulted in additional t-BCl reactivity for the alumina. This is in direct contradiction of the expected results based on conventional adsorption theory and practice, and suggests that the postulated catalytic reaction is in fact the method of t-BCl removal.

EXAMPLE 10

An isobutylene/isoprene solution containing a trace amount of t-BCl was prepared by adding 0.25 g t-BCl to 249.75 grams of a 75% isobutylene/25% isoprene mixture. Ten grams of a high surface area alumina (PECHINEY type A) was placed in a 300 cc bomb. After evacuation of the bomb, 101.5 grams of the t-BCl contaminated solution was added, and the bomb was sealed. The bomb was shaken for 15 minutes and allowed to stand at 22° C. for 70 hours. The composition of the solution before it was contacted with the alumina was:

| component | Concentration, wt % |
|---|---|
| Isobutylene | 74.1247 |
| Isoprene | 25.7646 |
| t-BCl | 0.0960 |
| Isobutane | 0.0117 |
| Butene-1 | 0.0028 |
| Diisobutylene | 0.0002 |

After 70 hours of contact with a lumina, GC analysis of the solution when compared with a GC analysis of the solution prior to contacting it with alumina, showed that the t-BCl peak, which appeared at retention time 16.45 minutes, had disappeared. Hence, the alumina is effective at removing trace amounts of t-butyl chloride from an isobutylene isoprene stream. The GC analysis further showed that there was very little dimer formation during the alumina treatment of the olefinic solution at the lower temperatures.

Based on the data obtained which appears in Table I, the alumina capacity in t-BCl removal can be represented by the following equation:

$$C = 96,375\ e^{-\frac{2646}{T^\circ K}}$$

where C is the t-butyl chloride capacity of the alumina in weight of t-BCl per 100 weight of alumina and T is the temperature of the t-BCl contaminated process stream in degrees Kelvin. Since the capacity of the alumina for t-BCl increases with temperature, the removal phenomenon is not merely an adsorption process, but involves a chemical reaction and therefore is a chemisorption process.

TABLE I
REMOVAL OF TBCL BY ALUMINA

| Type of Test | Exp. No. | Rx. Temp. °C. | Alumina Capacity | |
|---|---|---|---|---|
| | | | g tBCL/100 g Alumina | g HCL/100 g Alumina |
| Static | 1 | −22-20 | 2.71 | 1.07 |
| | | | 2.66 | 1.05 |
| | 2 | | 2.61 | 1.03 |
| Static | 3 | −12-10 | 3.18 | 1.25 |

TABLE I-continued
REMOVAL OF TBCL BY ALUMINA

| Type of Test | Exp. No. | Rx. Temp. °C. | g tBCL/100 g Alumina | g HCL/100 g Alumina |
|---|---|---|---|---|
| | 6 | | 3.76 4.34 | 1.48 1.71 |
| Static | 4 | 23-25 | 8.68 | 3.42 |
| | 5 | | 9.43 9.06 | 3.71 3.57 |
| Dynamic | 8 | 32 | 16.78 | 6.61 |
| Dynamic | 9 | 43 | 21.86 | 8.61 |
| Dynamic | 7A | 60-62 | 21.42 | |
| | 7B | | + 34.35 12.93 | 13.53 |

| Type of Test | Exp. No. | t BCL Conc., ppm, | | IC₄ = conc. |
|---|---|---|---|---|
| | | Start | Final | ppm |
| Static | 1 | 11,210 | 9,223 | 330 |
| | 2 | | 9,296 | 350 |
| Static | 3 | 11,210 | 8,885 | 576 |
| | 6 | | 8,030 | 644 |
| Static | 4 | 11,210 | 4,855 | 2,854 |
| | 5 | | 4,306 | 3,073 |
| Dynamic | 8 | 11,125 | 2,900 | |
| Dynamic | 9 | (11,215) | 410 | |
| Dynamic | 7A | 11,163 | 554 | |
| | 7B | 11,290 | 4,554 | |

What is claimed is:

1. In a methyl chloride slurry polymerization process for preparing butyl rubber from a monomer mixture which comprises an isoolefin and conjugated multiolefin, wherein the methyl chloride and unreacted monomer are separated from the butyl rubber by flashing in hot water and the recovered methyl chloride-monomer mixture is subsequently dried over alumina, thereby forming t-butyl chloride from the isoolefin, the dried methyl chloride and monomers being separated from one another by fractionation, the improvement which comprises treating the unreacted dried monomer to remove the said t-butyl chloride by again contacting the unreacted monomer with alumina for a time sufficient to remove the said t-butyl chloride.

2. The process according to claim 1 wherein the conjugated multiolefin is isoprene.

3. The process according to claim 1 wherein the isoolefin is isobutylene.

4. The process according to claim 1 wherein the unreacted monomer is contacted with the alumina at a temperature of about −40° C. to 120° C.

5. The process according to claim 1 wherein the unreacted monomer i.e. contacted with the alumina at an elevated temperature.

6. The process according to claim 1 wherein the unreacted monomer is contacted with the alumina at a temperature of about 20° C. to about 120° C.

7. The process according to claim 1 wherein the unreacted monomer is contacted with the alumina at a temperature of about 30° C. to about 140° C.

8. The process according to claim 1 wherein the unreacted monomer is contacted with the alumina at a temperature of about 40° C. to about 100° C.

9. The process according to claim 1 wherein the unreacted monomer is contacted with the alumina at a temperature of about 60° C. to about 80° C.

10. The process according to claim 2 wherein the isoolefin and isoprene which are present in the unreacted monomer are separated by fractionation, the said t-butyl chloride being concentrated in the isoprene stream, and the isoprene stream is contacted with the alumina.

11. The process according to claim 10 wherein the isoolefin is isobutylene.

12. In a process for preparing butyl rubber in a methyl chloride slurry process from a monomer mixture which comprises an isoolefin and conjugated multiolefin, wherein the methyl chloride and unreacted monomer are separated from the butyl rubber by flashing in hot water and the recovered methyl chloride-monomer mixture is subsequently dried over alumina, thereby forming a t-butyl chloride from the isoolefin, the dried methyl chloride and monomers being separated from one another by fractionation, the improvement which comprises treating the unreacted dried monomer to remove the said t-butyl chloride by again contacting the unreacted monomer with alumina at an elevated temperature for a time sufficient to remove the said t-butyl chloride.

13. The process according to claim 12 wherein the unreacted monomer is contacted with the alumina at a temperature of at least 30° C.

14. The process according to claim 12 wherein the unreacted monomer is contacted with the alumina at a temperature of at least 40° C.

* * * * *